United States Patent [19]

Harhen

[11] Patent Number: 5,702,348
[45] Date of Patent: Dec. 30, 1997

[54] DISPOSABLE ENDOSCOPIC SHEATH SUPPORT AND POSITIONING ASSEMBLY

[75] Inventor: E. Paul Harhen, Duxbury, Mass.

[73] Assignee: Vision-Sciences, Inc., Natick, Mass.

[21] Appl. No.: 685,704

[22] Filed: Jul. 24, 1996

[51] Int. Cl.⁶ .................................................. A61B 1/04
[52] U.S. Cl. ........................ 600/124; 600/121; 600/125
[58] Field of Search ................................ 600/121, 122, 600/123, 124, 125; 604/263, 96, 103, 163

[56] References Cited

U.S. PATENT DOCUMENTS

| | | | |
|---|---|---|---|
| 4,620,527 | 11/1986 | Adams, Jr. | 128/4 |
| 4,646,722 | 3/1987 | Silverstein et al. | 128/4 |
| 4,721,097 | 1/1988 | D'Amelio | 600/125 X |
| 4,907,395 | 3/1990 | Opie et al. | 53/434 |
| 4,991,564 | 2/1991 | Takahashi et al. | 600/123 X |
| 4,997,084 | 3/1991 | Opie et al. | 206/364 |
| 5,337,731 | 8/1994 | Takahashi et al. | 128/4 |
| 5,419,310 | 5/1995 | Frassica et al. | 128/4 |
| 5,520,607 | 5/1996 | Frassica et al. | 600/102 |

Primary Examiner—Beverly M. Flanagan
Attorney, Agent, or Firm—Seed and Berry LLP

[57] ABSTRACT

An endoscopic sheath support assembly for supporting a sheath in a substantially fixed position for installation and removal of an endoscope insertion tube. The support assembly has an elongated rigid support tube with an interior area, and the sheath is in the interior area. The support tube is releasably connectable to a vacuum source to create a partial vacuum to expand the sheath. The distal end of the support tube has a pair of opposing openings that are adjacent to the distal end of the sheath when the sheath is positioned in the support tube. A resilient sheath retaining sleeve sealably covers the opposing openings. The resilient sheath retaining sleeve is movable by the partial vacuum to a retaining position wherein portions of the sleeve extend through the openings and engage the distal end of the sheath to retain the distal end of the sheath in a substantially fixed position relative to the support tube. The sheath engaging sleeve is biased toward a released position when the partial vacuum in the interior area is terminated.

20 Claims, 2 Drawing Sheets

DISPOSABLE ENDOSCOPIC SHEATH SUPPORT AND POSITIONING ASSEMBLY

TECHNICAL FIELD

The present invention relates to endoscopy, and more particularly, to endoscopic assemblies to facilitate efficient installation and removal of a sheath from an endoscope.

BACKGROUND OF THE INVENTION

The use of endoscopes for diagnostic and therapeutic indications is rapidly expanding. To improve performance, endoscopes have been optimized to best accomplish their purposes. Therefore, there are upper endoscopes for examination of the esophagus, stomach, and duodenum; colonoscopes for examining the colon; angioscopes for examining blood vessels, bronchoscopes for examining the bronchi; laparoscopes for examining the peritoneal cavity; and arthroscopes for examining joint spaces. The discussion which follows will apply to all of these types of endoscopes.

Instruments known as bronchoscopes used to examine the interior of a patient's lungs are expensive and they must be sterile before beginning the endoscopic procedure to avoid introducing any bacteria, viruses, or other contaminants into the lungs. Endoscopic instruments to examine the rectum and sigmoid colon, known as flexible sigmoidoscopes, are also expensive, and they are used for a brief procedure (5-10 minutes) in a contaminated environment to screen symptomatic and asymptomatic patients for colon and rectal cancer. These conventional endoscopes and other types of endoscopes have experienced problems with respect to contamination of the endoscopes and the cleaning time necessary prior to subsequent endoscopic procedures. Ideally, endoscopes must be used rapidly and inexpensively to maintain the cost of the examinations at acceptable levels. As an example, a clinic would like to perform five sigmoidoscope examinations each hour.

A significant problem with allowing rapidly successive endoscopic examinations is the time necessary for adequate cleaning of the device. Although the endoscopes can be superficially cleaned in about 2-4 minutes, this relatively cursory cleaning may not be adequate for complete disinfection and it does not sterilize the instrument. A more complete cleaning requires on the order of 8-10 minutes and may still not allow for adequate cleaning, particularly in view of the increasing problems with contagious viruses, including HIV. In fact, federal regulations require that an endoscope be cleaned and then soaked in a chemical bath for 45 minutes before performing the next procedure. Even with the use of chemicals, and depending on the cleaning methods, adequate cleanliness may not be possible.

In the healthcare field, the problems of contaminated instruments transmitting disease from one patient to the next have generally been solved by making such instruments disposable. However, this approach is currently not economically feasible in the field of endoscopy because endoscopes are expensive instruments. U.S. Pat. No. 4,646,722 describes an endoscopic sheath that significantly resolves the problem of endoscope contamination. The sheath has a flexible tube that surrounds the elongated insertion tube of the endoscope, and the flexible tube has a transparent window in its distal end positioned in front of a viewing window of the endoscope's insertion tube. Channels that come into contact with a patient or a patient's bodily fluids, e.g., channels for taking biopsies, injecting air, or injecting water to wash the window of the sheath, are included with the sheath, so the channels extend parallel to the insertion tube such that the insertion tube is completely isolated from contamination by the bodily fluids.

Difficulties have been encountered in properly installing and removing the sheath on the endoscope's insertion tube without contaminating the endoscope, other equipment, or personnel using the equipment. U.S. Pat. No. 4,646,722 teaches providing the sheath in a rolled up configuration, placing the distal end of the sheath in contact with the distal end of the endoscope, and unrolling the sheath onto and along the length of the endoscope insertion tube. However, this rolling procedure is relatively time intensive to ensure proper alignment of the distal ends of the sheath and insertion tube. Rolling or even stripping a contaminated sheath from an endoscope is undesirable, particularly for relatively long insertion tubes, because a user must handle the soiled or contaminated sheath, and after touching the contaminated sheath, the user must then be very careful to avoid touching and contaminating the endoscope, other equipment, or other personnel.

U.S. Pat. No. 4,997,084 teaches a packaging system for a disposable elastomeric endoscopic sheath. The sheath is contained in an elongated flexible sheath bag, and the sheath is inflated in the bag so the insertion tube can be easily inserted into the sheath. The sheath is then deflated to tightly encase the insertion tube. This sheath inflation procedure for installation or removal of the insertion tube has experienced problems controlling the distal end of the sheath during installation, because the flexible sheath expands distally as well as radially, and the sheath's distal end tends to migrate, making proper installation of the insertion tube difficult. During installation, the viewing window in the distal end of the insertion tube must be aligned and positioned immediately adjacent to the window in the distal end of the sheath. Misalignment of the windows due to an ineffective installation procedure will result in glare or impaired vision.

Furthermore, the distal end of the insertion tube is typically positively locked or otherwise connected to the distal end of the sheath to ensure proper alignment. Creating this positive connection during installation of the endoscope typically requires a user to grasp the end of the sheath to secure its position for connection to the insertion tube. Removal of the insertion tube from the sheath also requires the user to grasp the distal end of the sheath to secure it in order to unlock or disconnect the sheath from the insertion tube. Grasping of the contaminated sheath by the user is undesirable because of the risk of contaminating other equipment and the like. Accordingly, the conventional sheath expansion technique for installation and removal of the endoscope insertion tube creates significant difficulty in controlling the distal end of the sheath to ensure proper alignment and to facilitate securing and releasing the distal end of the sheath from the distal end of the insertion tube.

SUMMARY OF THE INVENTION

The present invention provides a sheath support member for installation and removal of the sheath that overcomes the problems experienced by the conventional systems. A preferred embodiment of the present invention provides a sheath support assembly for supporting an endoscopic sheath in a substantially fixed position for installation and removal of an endoscope insertion tube. The sheath support assembly includes an elongated, substantially rigid support tube having an interior area extending between proximal and distal ends of the insertion tube. The support tube is sized to receive an endoscopic sheath within the interior area such that the sheath can be radially expanded from a contracted position. The support tube is connectable to the vacuum source to create a partial vacuum in the support tube and expand the sheath. A sheath retaining member is attached to the distal end of the support tube and is movable by the partial vacuum relative to the support tube between a released position and a sheath retaining position. When the partial vacuum is generated in the support tube, the sheath retaining member is moved to the retaining position wherein the sheath retaining member engages and holds the distal end of the sheath in a substantially fixed position relative to the support tube.

In the preferred embodiment, the support tube has a pair of opposing elongated openings in its distal end at a position adjacent to a distal end of the sheath when the sheath is positioned in the support tube. The sheath retaining member is an elastomeric sleeve mounted on a portion of the support tube, and the sleeve covers the elongated openings in the support tube's distal end. When the partial vacuum is generated in the support tube, the partial vacuum draws portions of the sleeve inwardly through the openings and moves the portions of the sleeve to the retaining position and into secure engagement with the distal end of the endoscope sheath.

DETAILED DESCRIPTION OF THE INVENTION

Figure 1:
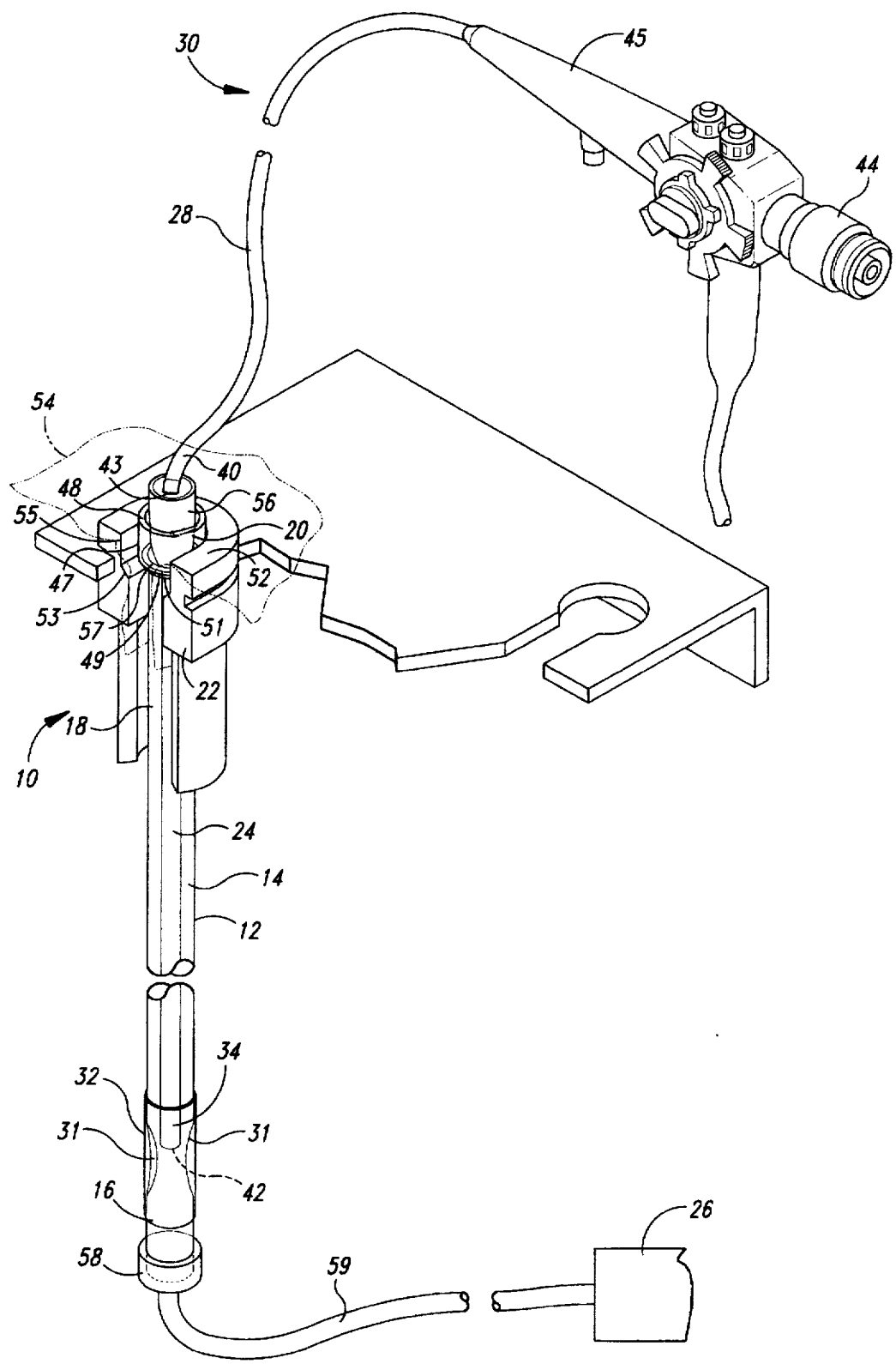
FIG. 1 is an isometric view of a sheath support assembly showing a preferred embodiment of the present invention, the assembly being shown mounted on a holding member with a sheath shown installed in the assembly, and a vacuum source connected to the assembly.

A preferred embodiment of a sheath support assembly 10 in accordance with the present invention is shown in the attached drawings for illustrative purposes. As best seen in FIG. 1, the sheath support assembly 10 includes a support tube 12 that defines an interior area 14 extending between a distal end 16 and a proximal end 18. The proximal end 18 is attached to a substantially rigid mouth structure 20 that is removably mountable in a holding assembly 22. The support tube 12 is shaped and sized to removably receive an endoscope sheath 24 through the mouth structure 20 and into the interior area 14. As discussed in greater detail below, the sheath support assembly 10 supports and retains the sheath 24 so as to facilitate the insertion and removal of a flexible insertion tube 28 of an endoscope 30.

The distal end 16 of the support tube 12 has an opening 25 that is attachable to a vacuum source 26. When the vacuum source 26 is activated, a partial vacuum is created within the interior area 14. The partial vacuum causes the flexible sheath 24 to expand radially to an expanded position having an enlarged cross-sectional area for easy installation or removal of the endoscope's insertion tube 28. The distal end 16 of the support tube 12 has a pair of openings 31 in the support tube's sidewalls. A sheath retaining sleeve 32 positioned on the support tube's distal end 16 covers the openings 31, and a portion of the retaining sleeve is adapted to be drawn into the interior area 14 to an retaining position when the partial vacuum is created in the support tube. The sheath retaining sleeve 32 engages a distal end 34 of the sheath 24 while the remaining portion of the sheath is radially expanded.

The distal end 34 of the sheath 24 has a viewing window 42 therein, and the endoscope's insertion tube 28 contains a conventional imaging system, for example a video system or the like, with a viewing window 43 at the distal end 40 of the insertion tube. The viewing window 43 on the insertion tube 28 must be positioned and retained immediately adjacent to the viewing window 42 in the sheath 24 when the insertion tube is inserted into the sheath. The imaging system is connected to an eyepiece 44 on a handle 45 of the endoscope 30 to allow a physician to see beyond the insertion tube's distal end 40 during an endoscopic procedure. Misalignment of the insertion tube's distal end 40 relative to the viewing window 42 on the sheath's distal end 34 can create glare, focus, or problems that impair visibility. Accordingly, the sheath support assembly 10 provides the flexible sheath retaining sleeve 32 to firmly grasp and retain the sheath's distal end 34 in a substantially fixed position for quick and accurate installation of the insertion tube 28 into the sheath 24, and for quick and clean removal of the insertion tube from the sheath.

As best seen in FIG. 1, the rigid mouth structure 20 is a generally cylindrical structure with sidewalls 47 defining an open proximal end 48 with a first diameter, and an inwardly tapering open distal end 49. The inwardly tapering distal end 49 defines a retaining shoulder 51 that connects to the proximal end 18 of the support tube 12. Accordingly, the outer diameter of the mouth structure 20 at the proximal end 48 is larger than the outer diameter of the distal end 49 of the mouth structure at the support tube 12. The retaining shoulder 51 is shaped and sized so the mouth structure simply fits into the holding assembly 22, which holds the sheath support assembly 10 in a generally vertical orientation.

In the preferred embodiment, the holding assembly 22 is a generally U-shaped member having opposing legs 52 that define a slot therebetween. Each of the legs 52 has an upper portion 55 spaced apart from the other a distance slightly greater than the outer diameter of the proximal end 48 of the mouth structure 20. A support flange 53 is integrally connected to the legs 52 below the upper portions 55, and the support flange extends inwardly to define a narrowed lower portion of the slot that is slightly larger than the outer diameter of the support tube 12. The mouth structure 20 is removably received into the slot of the holding assembly 20 and the retaining shoulder 51 is moved into engagement with the support flange 53 to snugly hold the sheath support assembly 10.

In the preferred embodiment, a disposable plastic drape 54 is positioned to cover the holding assembly 22 and to extend through the slot so the drape is sandwiched between the mouth structure 20 and the holding assembly 22. Accordingly, the holding assembly 22 is covered and protected from contamination during use of the sheath support assembly 10.

The mouth structure 20 retains the proximal end 56 of the sheath 24 at a position such that the distal end 34 of the sheath is located adjacent to openings 31 in the support tube's distal end 16. The mouth structure 20 includes an annular seal 57 that engages the sheath's proximal end 56 to form a generally airtight seal to maintain the partial vacuum within the support tube 16 upon activation of the vacuum source 26.

Figure 3:
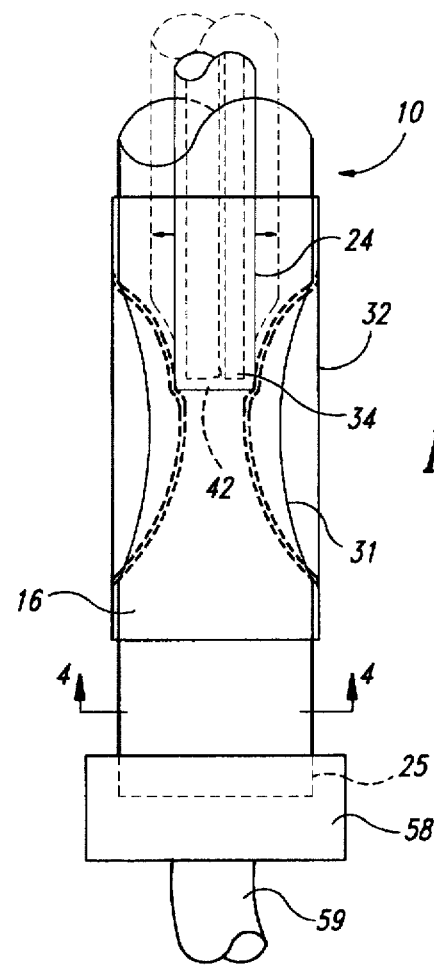
FIG. 3 is an enlarged side elevation view of a distal end of the assembly of FIG. 1 with a sheath engaging sleeve shown in solid in a released position, and shown in phantom in a retaining position engaging a distal end of the sheath.

As best seen in FIGS. 1 and 3, the opening 25 in the distal end 16 of the support tube 12 is sealably covered by a vacuum fitting 58 that is releasably attached to the sidewalls of the support tube. The vacuum fitting 58 has an aperture that communicates with the interior area 14 of the support tube 12, and the aperture is operatively connected to a vacuum hose 59 from the vacuum source 26. The support tube 12 and the sheath retaining sleeve 32 are made of air impervious material, so the partial vacuum in the interior area 14 created by the vacuum source 26 is maintained while the sheath 24 is installed and until the vacuum source is deactivated.

When the sheath 24 is in position with its distal end 34 adjacent to the distal end 16 of the support tube 12, the partial vacuum expands the sheath so as to increase its cross-sectional area substantially along the length of the sheath. The partial vacuum generated in the preferred embodiment is such that the sheath 24 expands radially within the support tube 12 to allow easy and quick installation of the endoscope insertion tube, but the radially expanded sheath does not contact the support tube. The support tube 12 is constructed of a substantially rigid plastic material that will not collapse when the partial vacuum is created.

Figure 2:
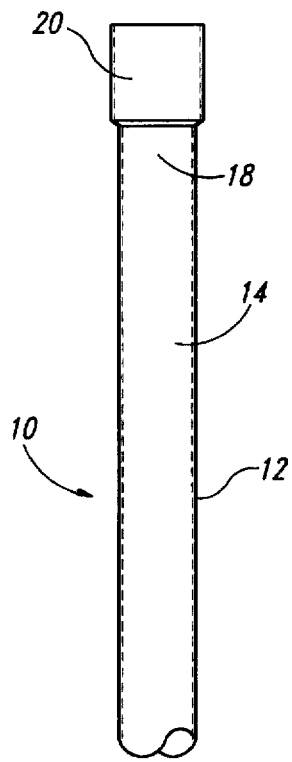
FIG. 2 is an enlarged side elevation view of the sheath support assembly of FIG. 1 removed from the holding member.
Figure 2:
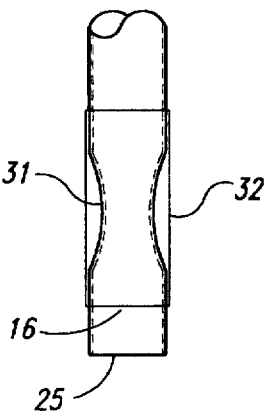
Figure 4:
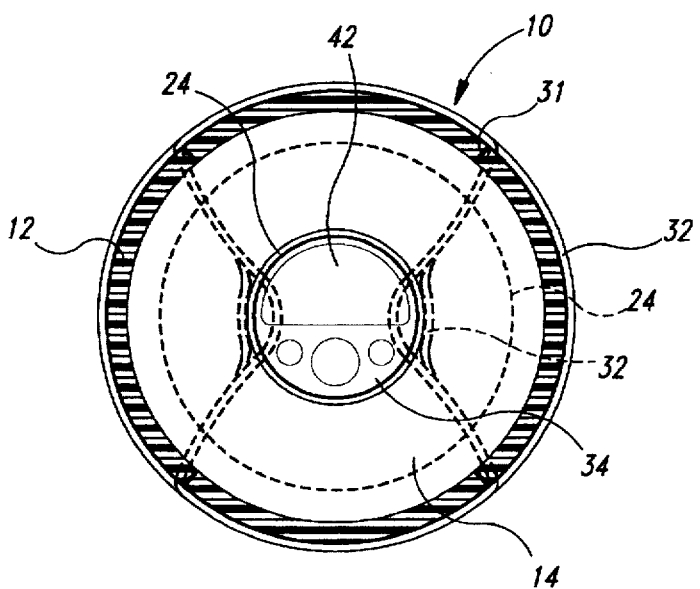
FIG. 4 is a cross-sectional view taken substantially along Line 4—4 of FIG. 3.

As best seen in FIGS. 2–4, the openings 31 in the distal end 16 of the support tube 12 are elongated, oval-shaped apertures that are each completely covered by the sheath retaining sleeve 32. The sheath retaining sleeve 32 of the preferred embodiment is a thin, resilient urethane sleeve, but a flexible, non resilient material may also be used as long as sufficient material is provided to allow the material to bow inwardly. The portions of the sleeve 32 covering the openings 31 are movable between an outward, released position illustrated in solid in FIGS. 2–4, and a contracted, retaining position shown in phantom. When the partial vacuum is created in the interior area 14, the portions of the sheath retaining sleeve 32 covering the openings 31 are stretched and drawn inwardly to the retaining position and partially wrap around the distal end 34 of the sheath 24.

The openings 31 are positioned so the distal end 34 of the sheath 24 is located slightly above an axis extending through the centers of each opening. As best seen in FIGS. 3 and 4, this location of the openings 31 allows a portion of the sheath retaining sleeve 32, when in the retaining position, to securely wrap around the exterior of the sheath's distal end 34 and to resist lateral movement of the distal end relative to the support tube 12 during installation or removal of the endoscope's insertion tube 28 (FIG. 1). A lower portion of the sheath retaining sleeve 32 is drawn inwardly by the partial vacuum and extends under the sheath's distal end 34. This lower portion of the sheath retaining sleeve 32 blocks the sheath's distal end 34 from moving axially in the distal direction. Accordingly, the sheath engaging sleeve 32 securely holds the distal end 34 of the sheath 24 in a substantially fixed position within the support tube 12.

The sheath retaining sleeve 32 is biased toward the released position so when the partial vacuum in the support tube 12 is terminated, the sheath retaining sleeve 32 moves from the retaining position to the released position, thereby releasing the distal end 34 of the sheath 24. Termination of the partial vacuum also allows the resilient sheath 24 to contract around the insertion tube 28 so the resulting sheathed insertion tube can be removed from the support tube 12 as a unit.

In one embodiment, the sheath support assembly 10 for use with a bronchoscope has a resilient, transparent urethane sheath retaining sleeve 32 having a durometer of 80 A and a thickness of approximately 0.10 inches. This sheath retaining sleeve 32 moves to the retaining position when the vacuum source 26 generates a partial vacuum of approximately 13 inches of mercury. The support tube 12 and the sheath retaining sleeve 32 are transparent so the physician can see the endoscope sheath 24 and insertion tube 28 within the support tube during the installation and removal procedure.

In the preferred embodiment, the sheath support assembly 10 is disposable and it is sized for a selected type of endoscope sheath 24. Accordingly, the sheath support assembly 10 and the sheath 24 can be combined, packaged, and delivered in a "ready-to-use" package. The sizes, dimensions, and materials of the embodiment discussed above are provided for purposes of illustration. For example, the size, shape, and number of the openings in the support tube's distal end 16 can be varied to increase or decrease the amount of contact between the sheath retaining sleeve 32 and the sheath's distal end 34. In addition, the sheath retaining sleeve 32 can be constructed of a material that is more resilient or less resilient to provide the desired degree of engagement and retention of the sheath's distal end 34 during the insertion or removal of the endoscope insertion tube 28. The sheath retaining sleeve 32 may also be integrally formed with a resilient support tube 12 as long as the portion forming the sheath retaining sleeve 32 is made more resilient such as by reducing the walls thickness of the tube 12.

Use of the sheath support assembly 10, for example, includes placing the sheath 24 into the support tube 12 through the mouth structure 20, and forming a seal between the sheath's proximal end 56 and the mouth structure. The mouth structure 20 is inserted into the holding assembly 22 (FIG. 1), and the support tube 12 hangs vertically from the holding assembly. The vacuum fitting 58 is connected to the open distal end 16 of the support tube 12. The vacuum source 26 is activated, thereby creating the partial vacuum within the support tube's interior area 14. The sheath retaining sleeve 32 is drawn to the retaining position and securely engages the sheath's distal end 34 as the remainder of the sheath is expanded.

The insertion tube 28 is then inserted into the sheath 24 so the distal end 40 of the insertion tube 28 is properly positioned immediately adjacent to the viewing window 43 of the sheath 24. The vacuum source 52 is then deactivated, terminating the partial vacuum, and allowing the sheath retaining sleeve 32 to return to the released position and the sheath 24 to contract around the insertion tube 28. The endoscope 30 and sheath 24 are then removed as a unit from the support tube 12 and used to perform a selected endoscopic procedure, which results in contaminating the sheath 24.

After the endoscopic procedure is completed, the contaminated sheath 24 and insertion tube 28 are inserted back into the support tube 12 through the mouth structure 20 so the distal end 34 of the sheath is adjacent to the sheath retaining sleeve 32. The vacuum source 26 is activated, creating the partial vacuum, thereby collapsing the sheath retaining sleeve 32 around the sheath's distal end 40 and securely holding it in place. The insertion tube 28 is then removed from the sheath 24, leaving the contaminated sheath in the sheath support assembly 10. The sheath support assembly 10 and contaminated sheath are removed from the holding assembly 22 and disposed of as a unit in a proper waste receptacle. Accordingly, the physician or technician does not need to touch the contaminated sheath after the endoscopic procedure to remove it from the endoscope or to dispose of it.

Numerous modifications and variations of the sheath support assembly disclosed herein will occur to those skilled in the art in view of this disclosure. For example, the openings 31 in the support tube's distal end could be covered by a flexible and deflectable material other than a sleeve that fits around the support tube. Therefore, it is to be understood that the modifications and variations, and equivalents thereof, may be practiced while remaining within the spirit and the scope of the invention as defined by the following claims.

What is claimed is:

1. A sheath support assembly for use with an endoscopic sheath, the sheath having first proximal and distal ends, the support assembly being releasably connectable to a vacuum source, comprising:
    a support tube having an interior area extending between second proximal and distal ends, the interior area being sized to contain a portion of the sheath therein, the support tube being connectable to the vacuum source to create a partial vacuum in the support tube, the partial vacuum being sufficient to expand the portion of the sheath in the interior area to an expanded position; and
    a sheath engaging member attached to the support tube adjacent the distal end of the sheath when a sheath is inserted in the support tube, the sheath engaging member being movable by the partial vacuum between a released position and a retaining position, the sheath engaging member being moved from the released position to the retaining position when the partial vacuum is generated to retain the distal end of the sheath in a substantially fixed position relative to the support tube.

2. The sheath support assembly of claim 1 wherein the sheath engaging member is biased toward the released position.

3. The sheath support assembly of claim 1 wherein the distal end of the support tube has an aperture therein, and the sheath engaging member is an elastic member covering the aperture.

4. The sheath support assembly of claim 3 wherein the sheath engaging member is a sleeve mounted on the support tube.

5. The sheath support assembly of claim 1 wherein the support member has two apertures therein, and the two apertures are sealably covered by portions of the sheath engaging member, the portions of the sheath engaging member being movable into the interior area relative to the two apertures to engage the distal end of the sheath when the partial vacuum is generated in the support tube.

6. The sheath support assembly of claim 5 wherein the two apertures are located on the support tube opposite each other.

7. The sheath support assembly of claim 5 wherein the sheath engaging member is a sleeve mounted on the support tube.

8. The sheath support assembly of claim 1 wherein the support tube is a substantially rigid cylindrical member made of substantially air impervious material.

9. The sheath support assembly of claim 1 wherein the second proximal end of the support tube includes a seal positioned to sealably engage the sheath when the sheath is positioned in the support tube.

10. An endoscope sheath and sheath support assembly for use with an endoscope, the endoscope having an insertion tube, the sheath support assembly being connectable to a vacuum source, comprising:
    a sheath having a proximal end and a distal end, the sheath being expandable to an expanded position to receive the endoscope insertion tube so a distal end of the insertion tube is positioned adjacent to the distal end of the sheath; and
    a sheath support assembly removably containing a portion of the sheath, the sheath support assembly including:
    an elongated support tube with an interior area extending between proximal and distal ends of the support tube, the support tube being connectable to the vacuum source;
    a sheath engaging member attached to the support tube adjacent the distal end of the sheath when a sheath is inserted in the support tube, the sheath engaging member being movable by a partial vacuum between a released position and a retaining position, the sheath engaging member being moved from the released position to the retaining position when the partial vacuum is generated in the support tube to retain the distal end of the sheath in a substantially fixed position relative to the support tube.

11. The endoscope sheath and sheath support assembly of claim 10 wherein the sheath engaging member is biased toward the released position.

12. The endoscope sheath and sheath support assembly of claim 10 wherein the distal end of the support tube has an aperture therein, and the sheath engaging member is an elastic member covering the aperture.

13. The endoscope sheath and sheath support assembly of claim 10 wherein the sheath engaging member is a sleeve mounted on the support tube.

14. The endoscope sheath and sheath support assembly of claim 10 wherein the support member has two apertures therein, and the two apertures are sealably covered by portions of the sheath engaging member, the portions of the sheath engaging member being movable into the interior area relative to the two apertures to retain the distal end of the sheath in a substantially fixed position relative to the support tube.

15. The endoscope sheath and sheath support assembly of claim 14 wherein the two apertures are located on the support tube opposite each other.

16. The endoscope sheath and sheath support assembly of claim 14 wherein the sheath engaging member is an elastomeric sleeve mounted to the support tube.

17. The endoscope sheath and sheath support assembly of claim 10 wherein the proximal end of the support tube includes a seal positioned therein that sealably engages the proximal end of the sheath.

18. A method of inserting an insertion tube of an endoscope into an endoscopic sheath, the sheath having proximal and distal ends, comprising the steps of:
    providing a sheath support member having a support tube with an open proximal end, a distal end, and an interior area extending between the proximal and distal ends;
    inserting the sheath into the interior area of the support tube, the support tube having a sheath engaging member positioned adjacent to the distal end of the sheath, the sheath engaging member being movable relative to the support tube between a radially outward released position and a radially inward retaining position;
    connecting a vacuum source to the support tube and creating a partial vacuum in the interior area;
    moving the sheath engaging member with the partial vacuum from the released position to the retaining position and engaging the distal end of the sheath;

retaining the distal end of the sheath with the sheath engaging member in a substantially fixed position relative to the support tube; and inserting the insertion tube into the sheath.

19. The method of claim 18 further including the steps of terminating the partial vacuum in the support tube, moving the sheath engaging member to the released position to disengage the distal end of the sheath, and removing the sheath and endoscope as a unit from the sheath support member.

20. The method of claim 19 further including the steps of performing an endoscopic procedure after removing the sheath and endoscope as a unit, inserting the sheath and endoscope into the support tube after the endoscopic procedure, activating the vacuum source when the sheath engaging member is in the released position and creating a partial vacuum in the interior area, moving the sheath engaging member with the partial vacuum to the retaining position and engaging the distal end of the sheath, and removing the insertion tube from the sheath.

* * * * *